United States Patent [19]

Keyes et al.

[11] Patent Number: 4,762,738
[45] Date of Patent: Aug. 9, 1988

[54] MEANS FOR DISPOSAL OF ARTICLES BY FLUSHING AND OSTOMY POUCHES PARTICULARLY SUITED FOR SUCH DISPOSAL

[75] Inventors: Denis E. Keyes, Staten Island; Marvin S. Aronoff, New York, both of N.Y.

[73] Assignee: E. R. Squibb & Sons, Inc., Princeton, N.J.

[21] Appl. No.: 944,891

[22] Filed: Dec. 22, 1986

[51] Int. Cl.[4] .................................... B32B 7/02
[52] U.S. Cl. ........................ 428/36; 604/332; 252/90
[58] Field of Search .................. 604/332; 252/90; 428/36

[56] References Cited

U.S. PATENT DOCUMENTS

| | | | |
|---|---|---|---|
| 2,850,471 | 9/1958 | Klein | 252/90 X |
| 3,089,493 | 5/1963 | Galindo | 128/283 |
| 3,186,869 | 6/1965 | Friedman | 252/90 X |
| 3,198,740 | 8/1965 | Dunlop et al. | 252/90 |
| 3,339,546 | 9/1967 | Chen | 128/156 |
| 3,561,447 | 2/1971 | Alexander | 128/290 |
| 3,654,929 | 4/1972 | Nilsson et al. | 128/287 |
| 3,661,695 | 5/1972 | Berlinger | 161/151 |
| 3,692,725 | 9/1972 | Duchane | 260/29.6 BM |
| 3,705,659 | 12/1972 | Mackle | 215/1 C |
| 3,707,430 | 12/1972 | Costanza et al. | 161/123 |
| 3,790,067 | 2/1974 | Scheier | 229/55 |
| 3,793,233 | 2/1974 | Rose et al. | 252/547 |
| 3,808,165 | 4/1974 | Duchane | 260/29.6 BM |
| 3,881,210 | 5/1975 | Drach et al. | 15/104.93 |
| 3,886,112 | 5/1975 | Waston et al. | 260/33.4 R |
| 3,951,893 | 4/1976 | Gander | 260/23 AR |
| 4,035,540 | 7/1977 | Gander | 428/198 |
| 4,062,451 | 12/1977 | Gander | 206/524.2 |
| 4,133,779 | 1/1979 | Hellyer et al. | 252/547 |
| 4,261,066 | 4/1981 | Belz | 4/222 |
| 4,316,824 | 2/1982 | Pancheri | 252/551 |
| 4,333,464 | 6/1982 | Nakano | 128/290 R |
| 4,372,311 | 2/1983 | Potts | 128/287 |
| 4,387,712 | 6/1983 | Briggs et al. | 604/333 |
| 4,460,363 | 7/1984 | Steer et al. | 604/336 |
| 4,490,145 | 12/1984 | Campbell | 604/333 |
| 4,503,098 | 3/1985 | Potts | 427/394 |
| 4,551,490 | 11/1985 | Doyle et al. | 524/22 |
| 4,620,999 | 11/1986 | Holmes | 428/35 |
| 4,692,494 | 9/1987 | Sonenstein | 525/57 |
| 4,762,454 | 10/1973 | Wilkins | 150/1 |

FOREIGN PATENT DOCUMENTS

| | | |
|---|---|---|
| 10171 | 8/1981 | European Pat. Off. . |
| 64044 | 11/1983 | European Pat. Off. . |
| 80/1374 | 7/1980 | PCT Int'l Appl. . |
| 1271424 | 4/1972 | United Kingdom . |
| 1312370 | 4/1973 | United Kingdom . |
| 2083762 | 2/1985 | United Kingdom . |
| 2122090 | 8/1985 | United Kingdom . |

*Primary Examiner*—Nancy A. B. Swisher
*Attorney, Agent, or Firm*—Lawrence S. Levinson; Stephen B. Davis

[57] ABSTRACT

Flexible, soft objects such as ostomy pouches, wound dressings, bandages, diapers, etc. can be flushed down a conventional toilet by covering the article with a sheet of material which rapidly becomes slimy or exudes a slimy material on contact with the water in a toilet bowl or by adding such materials directly to the bowl. An ostomy pouch constructed from materials particularly suited for disposal in a toilet bowl is also disclosed. The pouch is constructed from laminates of water swellable, cold water insoluble films and water resistant tissue paper.

35 Claims, 2 Drawing Sheets

MEANS FOR DISPOSAL OF ARTICLES BY FLUSHING AND OSTOMY POUCHES PARTICULARLY SUITED FOR SUCH DISPOSAL

BACKGROUND OF THE INVENTION

At the present time, commercially available disposable articles such as ostomy pouches, diapers, bandages, sanitary napkins, tampons, etc., are disposed of by placing the soiled article in a garbage receptacle where it is collected on a daily, bi-weekly, or other regular basis. This method of disposal while not totally convenient is particularly awkward when the user is away from home, for example, at work or at a public facility. Clearly, it would be a benefit to provide a means for disposing of such articles by flushing in a conventional toilet. However, the user must be confident that the article will be flushed and pass through the plumbing system. The following are previous examples of suggestions for accomplishing these results.

Kiefer in European Pat. No. 10,171B discloses a flushable, disintegratable ostomy pouch made from a multi-layer foil. The inner layer which contacts the body waste is a water-insoluble film-forming material such as polyethylene. The middle layer is of a water soluble material such as polyvinyl alcohol or partially saponified polyvinyl acetate. The outer layer may have water-repellent characteristics and be a material which disintegrates in water when additionally subjected to mechanical means such as kraft paper.

Samways et al. in British Pat. No. 2,083,762 B disclose a disposable ostomy pouch formed of a composite sheet material comprising an outwardly-presented mechanically strong, backing layer which has good tensile strength and cohesion when dry but which is dissolved or dispersed when immersed in mildly turbulent water and an inwardly-presented mechanically weak but water-impermeable layer. The outer layer can be a low wet strength paper or preferably a plastic film such as polyethylene oxide or polyvinyl alcohol. The polyvinyl alcohol may be plasticized and may be a hot-water soluble grade. Materials suitable for forming the water-impermeable layer include polyvinylidene chloride, Saran, nitrocellulose, waxes, pressure sensitive adhesive for example a solution of rubber latex in an organic solvent, etc.

Galindo in U.S. Pat. No. 3,089,493 discloses a colostomy bag having a disposable liner. The disposable bag consists of an outer layer of paper coated with a rather insoluble material.

Scheier in U.S. Pat. No. 3,790,067 discloses a container having an inner layer of water-insoluble material and an outer layer of water soluble polymeric material such as polyvinyl alcohol. The outer layer comprises the load-bearing member and the inner layer is sufficiently thin to be shredded under normal atmospheric forces or by the weight of the material in the container.

Watson et al. in U.S. Pat. No. 3,886,112 disclose a plastic composition consisting of partially hydrolyzed polyvinyl alcohol resin with a gelling amount of a water soluble borate salt. The material is insoluble in small volumes of water or body fluids but soluble in large volume. It can be formed into film and various shaped objects such as sanitary napkin barrier films.

Wilkins in U.S. Pat. No. 3,762,454 discloses a disposable garbage container which will degrade in situ in a garbage dump. The container is made of a laminate of cold water soluble polyvinyl alcohol and hot water soluble polyvinyl alcohol.

Potts in U.S. Pat. No. 4,372,311 disclose disposable articles made from water soluble polymers coated with a degradable water-insoluble polymer suitable for use in diapers, catamenial devices, sanitary napkins, bandages, etc. The water soluble polymer is selected from poly-(alkylene oxide), hydroxyethyl cellulose, hydroxypropyl cellulose, polyvinyl alcohol, polyvinyl pyrrolidone, etc. The degradable water-insoluble polymer is selected from a cyclic ester polymer, a poly ($\beta$-hydroxy butyrate), dialkanoyl polymers, and ethylene polymers.

Holmes in U.S. Pat. No. 4,620,999 discloses a disposable bag made from 3-hydroxybutyrate or a laminate of 3-hydroxybutyrate and polyvinyl alcohol or polyethylene oxide. Basic material is provided to modify the pH of the bag contents to at least 12 so that the bag will disintegrate and can be flushed.

Oberstein in No. WO 80/01374 discloses a flushable bedpan made of plastic material that dissolves in water of a temperature of less than 60° F. but will not be dissolved by water or liquid above 60° F. The water soluble plastic material is a modified hydroxypropyl cellulose.

Procter & Gamble Co. in British Pat. No. 1,312,370 discloses short fibered airfelt pads used as the absorbent layers in disposable articles such as diapers, sanitary napkins, etc., which are disposable by toilet flushing.

National Polymers and Chemical Corp. in British Pat. No. 1,271,424 disclose disposable bedpan liners consisting of a base film 11 of a water disintegratable or cold water soluble polyvinyl alcohol polymerization product, a thin water-insoluble coating 12, and a single ply tissue paper 13 of toilet tissue grade. In another embodiment, the other side of base film 11 is covered with a layer of paper which is strong when dry but of weak wet strength.

SUMMARY OF THE INVENTION

This invention is directed to means and methods enabling the disposal of various articles by flushing in a conventional toilet system. The means involves providing a slimy layer which lubricates and/or softens the article thus assuring its passage through the plumbing system. Suitable means include wrapping or enclosing the article within a material that becomes slimy or exudes a slimy material when in contact with the water in a toilet bowl. This result can also be accomplished by coating the article with a lubricating and/or softening substance prior to placement within the toilet bowl or adding such substances directly to the toilet bowl just prior to flushing.

Another object of this invention is the construction of an ostomy pouch from materials selected so that the ostomy pouch can be reliably disposed by flushing in a conventional toilet. The pouch is formed of materials which in use maintain their structural integrity. However, after flushing through the conventional toilet, the pouch softens and becomes flexible so that it can break up and tear on its way to a municiple sewer system or eventually degrade within a septic system.

The pouch material is preferably a laminate of a water resistant tissue paper layer and a layer of a hot water soluble film such as polyvinyl alcohol film. When formed into the ostomy pouch configuration, the hot water soluble film will be the interior pouch layer.

Another aspect of this invention is such flushable ostomy pouch having a deodorizing filter for the release of flatus that builds up within the pouch. The filter is located in an upper portion of the pouch above the stomal opening. The filter is isolated from the remainder of the pouch by means of a heat seal except for a gap that permits gas to travel into the filter area. The heat seal prevents any material that flakes off from the filter from falling into the waste collection portion of the pouch and from falling onto the stoma that protrudes into the pouch.

According to a further aspect of this invention, the flushability of the ostomy pouch formed from the laminate described above is enhanced by use of the means described above.

DETAILED DESCRIPTION OF THE INVENTION

This invention is directed to means and methods which enable the disposal of various medically related articles by flushing in conventional toilet systems. The articles can be any relatively flexible, soft objects such as ostomy pouches, wound dressings, bandages, diapers, sanitary napkins, tampons, etc. This result is accomplished by totally covering the article with a slimy layer which lubricates the article so that it can slip past close contact points and around bends in going from the toilet bowl to the trap, through the trap, and into the waste line. The slimy layer also helps wet down the surface of the article increasing its softness and flexibility and thus enhancing its flushability.

A convenient and preferred way to create such slime layers is to cover or enclose the article to be flushed with a dry film or sheet of material which rapidly becomes slimy or exudes a slimy material on contact with the water in a toilet bowl. For example, the article to be flushed is wrapped within a sheet of such material or placed within a bag or sleeve formed from such material.

Another method is to add liquid or solid surfactants and/or softening agents directly to the water within the toilet bowl or water tank in a continuous manner. Another method is to coat the surface of the article with such surfactants and/or softening agents. Suitable surfactants and/or softening agents include a 1:1 stearic acid monoethanolamide; glycerol; blends of ammonium alkyl ether sulfate, ammonium alkyl sulfate, sodium alkyl glyceryl ether sulfonate, and coconut alcohols as taught by Rose et al. in U.S. Pat. No. 3,793,233; and blends of magnesium salts of ethoxylated, sulfated coconut alcohols and long chain alkyl sulfates, dimethylalkyl amine oxides, ethoxylated alcohols and/or phenols as taught by Hellyer et al. in U.S. Pat. No. 4,133,779 and Pancheri in U.S. Pat. No. 4,316,824. Suitable commercially available surfactant compositions include various dishwashing detergents such as Ivory® and Joy® both available from Procter and Gamble Co., Cincinnati, Ohio. Thus, flushability is enhanced by placing from about $\frac{1}{4}$ ounce to about an ounce of dishwashing detergent on the exposed surface of the article.

Figure 1:
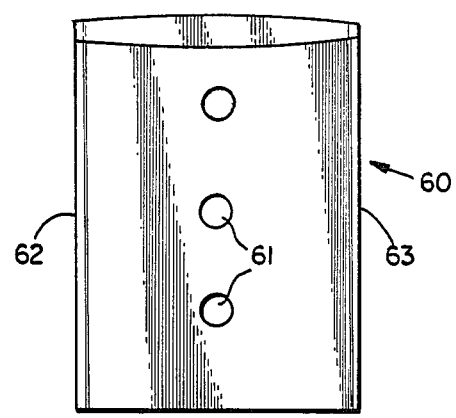
FIG. 1 is a perspective view of a bag formed of materials that will provide a lubricating effect to an article placed therein. The bag is shown in its open configuration prior to insertion of the article to be flushed.

According to the preferred method, the article to be flushed is wrapped or placed within a sleeve or bag formed of material which will soften and form a slimy layer on the article when contacted with the water in a conventional toilet bowl. FIG. 1 shows a bag 60 constructed to be slightly larger than the article to be flushed. The bag is sealed on three sides with an open mouth. The bag is constructed by folding a sheet of suitable material and heat sealing along the two side edges 62 and 63. When folded over, one wall can be slightly longer so as to aid the user in opening the bag. Bag 60 can include one or more apertures 61 in either or both bag walls so as to enable trapped air to escape from the bag. Alternatively, the bag can be constructed from materials of an open mesh structure thereby obviating the need for apertures. While a bag 60 has been shown, the same material can be formed into a sleeve by sealing the material into a tube configuration and then cutting to the desired length.

Material suitable for use in forming bag 60 or the alternate sleeve or wrap include polyvinyl alcohol, polyethylene oxide, polypropylene oxide, polyethylene glycol, co-polymers of ethylene oxide and propylene oxide, carboxymethylcellulose, hydroxyethylcellulose, hydroxypropylcellulose, polyacrylamides, surfactant and/or softening agent impregnated tissue paper, and highly absorbent tissue paper which is preferred in some toilet systems of the washdown type which lack a vortex. Among these materials, the preferred in vortex toilet systems is a film of cold water soluble polyvinyl alcohol of about 0.6 mils thickness. A suitable commercially available cold water soluble polyvinyl alcohol film is available with an embossed pattern from Nippon Gohsei under their tradename Hi-Selon AH 15. Embossing results in a film of greater flexibility and softness.

Of course, in toilet systems prone to clogging, it may be desirable to both place the article to be flushed within bag 60 or an equivalent sleeve and then also add solid or liquid surfactants and/or softening agents to the toilet bowl prior to flushing. Alternatively, if the article within bag 60 fails to clear the bowl or trap on the first flush, the surfactant and/or softening agent composition can then be added to the toilet bowl prior to the second flush.

The means and methods described above are useful in flushing various articles including conventional ostomy pouches. However, such pouches are normally formed from hydrophobic polymeric materials or laminates and after flushing would tend to clog residential and commercial waste disposal systems. Also, their accumulation would eventually impede the function of septic systems. Thus, there is a need for an ostomy pouch which after flushing will break apart or tear into small pieces on its passage through the waste disposal system or will eventually degrade by natural processes.

Figures 2, 3:
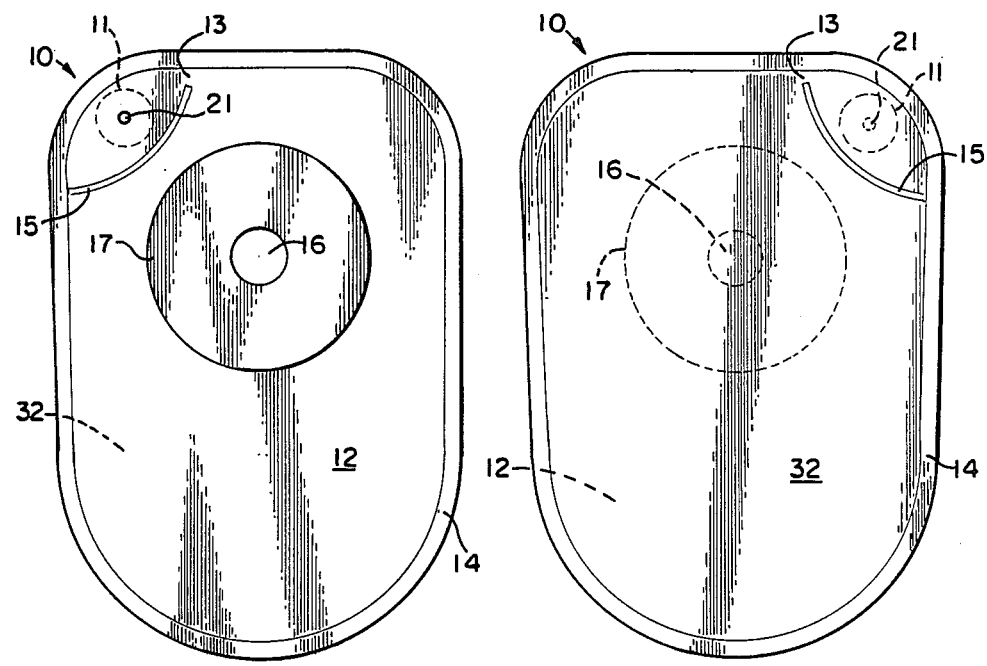
FIG. 2 is a front view of an ostomy pouch particularly suited for disposal by flushing as it would be applied to the body of the user.
FIG. 3 is a front view of the rear panel of such ostomy pouch.

Suitable ostomy pouches which accomplish these results are shown in FIGS. 2 to 8. The flushable ostomy pouch 10 of this invention as shown in FIGS. 2 and 3 consists of front panel 12 and rear panel 32 heat sealed around their periphery to each other by the bond 14. The term front panel is used to designate that portion of the pouch which in use is closest to the body.

Figure 6:
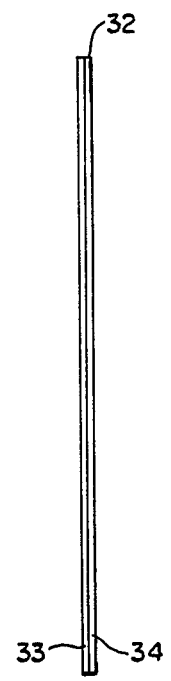
FIG. 6 is a side view of the rear panel of such ostomy pouch in greatly enlarged detail prior to its being joined to the front panel.

As best shown in FIG. 2, the front panel includes an opening 16 which functions as a starter hole. The user enlarges this opening by cutting so as to fit the pouch over and around the stoma. Of course, the pouch could be provided with pre-cut openings of various sizes. The stoma can thus protrude into the interior of the pouch. Front panel 12 is formed as a laminate of layers 18 and 19 and as best shown in FIG. 6 rear panel 32 is a laminate of layers 33 and 34. Layers 19 and 33 are to the exterior of the pouch when the front and rear panels are joined. Thus, layers 18 and 34 will constitute the pouch interior.

Pouch 10 in order to be disposable by flushing must be soft and pliable or capable of becoming soft and pliable when contacted with the water in the toilet bowl. However, at the same time, pouch 10 must be capable of maintaining its structural integrity during the normal period of use and must be able to support the normal weight of fecal material that will be discharged into the pouch. For a closed end colostomy pouch, the period of use can extend from several minutes to about 24 hours and the load of fecal material can be as much as about 250 grams. The pouch must maintain its integrity at body temperature and in the presence of moisture within the fecal material and perspiration that could permeate the pouch from the exterior. Also, the materials employed must result in a pouch having adequate odor barrier properties during use and the materials must be capable of being sealed so as to form the completed pouch. The cost and commercial availability of the materials are also important.

In addition to these properties for the overall pouch, material 19 which contacts the body of the user should feel comfortable and be non-irritating against the skin. Exterior material 33 which contacts the clothing of the user, should be relatively friction free so as to minimize any pulling on the pouch by clothing which could accidently dislodge the pouch from the body.

Suitable materials for interior pouch layers 18 and 34 include films which are water swellable but cold water insoluble such as hot water soluble polyvinyl alcohol, which is preferred, amylose films, cross-linked polyacrylamides, and block copolymers of ethylene oxide and propylene oxide. Water repellant tissue paper is the preferred material for body contacting layer 19 and water repellant tissue paper or an embossed film of cold water soluble polyvinyl alcohol are the preferred materials for clothing contacting outer pouch layer 33.

Figure 4:
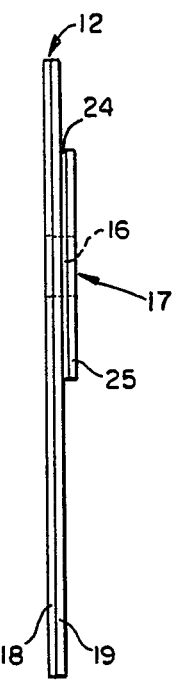
FIG. 4 is a side view of the front panel of such ostomy pouch in greatly enlarged detail prior to its being joined to the rear panel.

Attaching means 17 is included on the front pouch panel surrounding the starter hole 16 for attaching the pouch directly or indirectly to the body of the user. Preferably, as shown in the figures, attaching means 17 also has a starter hole 16 and is affixed to the front panel so that the starter holes are aligned. As best shown in FIG. 4, attaching means 17 includes a layer of pressure sensitive medical grade adhesive 24 that is capable of forming a bond with the skin of the user of sufficient strength to hold the pouch in place for from several hours to one or more days. The body contacting surface of adhesive layer 24 is covered prior to use by a sheet of silicone coated release paper 25.

Figure 5:
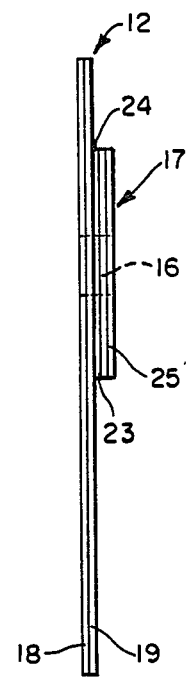
FIG. 5 is a side view of a modified front panel suitable for such ostomy pouch in greatly enlarged detail prior to its being joined to the rear panel.

As shown in FIG. 4, the adhesive layer 24 can be bonded directly to the surface of tissue paper layer 19 by a combination of heat and pressure. Alternatively, as shown in FIG. 5, a backing film layer 23 can be interposed between adhesive layer 24 and tissue paper layer 19. Preferably, film layer 23 is of a heat bondable or sealable material such as hot water soluble polyvinyl alcohol or ethylene vinylacetate. In this case, a seal using heat, moisture, and pressure is made through the front panel laminate thus bonding layer 23 onto layer 19.

Figure 7:
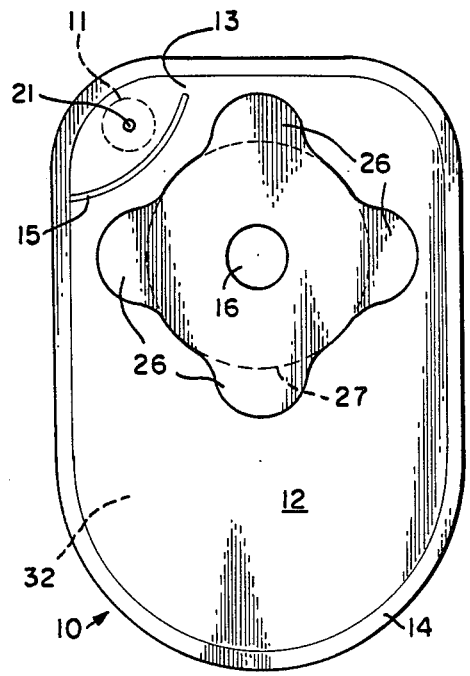
FIG. 7 is a front view of an ostomy pouch also suited for disposal by flushing and having a modified adhesive faceplate. This view shows the pouch as it would be applied to the body of the user.

FIG. 7 shows an alternate construction wherein the elements of attaching means 17 are not circular but include four extensions or tabs 26. Again, attaching means 17 includes an adhesive layer 24 and an optional backing film layer 23 of heat bondable or sealable material. In this embodiment, a heating tool having approximately the same diameter as that used in forming the pouch of FIGS. 2-6 is employed. Thus, the tabs 26 are not attached to the front panel and the user can place his finger behind the tabs to press the pouch onto the body. At the same time, the area of adhesive attachment to the body is increased so as to increase the security of the pouch on the body of the user. The periphery of the area of bonding between layers 19 and 23 or 24 is represented by the dashed line 27 in FIG. 7.

As shown in FIG. 2, front panel 12 can also include one or more perforations 21 which are placed to overlie a layer of deodorizing filter material 11. Of course, the perforations could be made in the rear panel in which case the flatus gas would be vented away from the body of the user.

Material 11 preferably contains activated carbon as a gas adsorbing and deodorizing agent. One type of suitable material is a sheet of foamed open-cell non-woven synthetic polymeric material, for example, polyurethane, having a large number of activated carbon particles distributed over one of its major surfaces. Such a material is commercially available under the tradename Bondina. Another type of suitable deodorizing material is a felt pad or paper impregnated with activated carbon in fine particulate form. Various types of such carbon cloths and papers are commercially available.

As shown in FIGS. 2, 3, 7 and 8, a bar weld 15 of an arc configuration separates filter 11 from the main portion of the pouch. A gap 13 of from about ⅛ to about ¼ inch is provided between one end of the weld 15 and the outer peripheral pouch weld 14 that joins front panel 12 and rear panel 32. The other end of weld 15 passes through or ends at the peripheral pouch weld 14. The gap is of sufficient size so that gas passing from the stoma into the pouch can travel into contact with filter 11. The gas then passes through filter 11 where it is deodorized and exits the pouch through apertures 21 in front panel 2. The location of gap 13 at the upper end of the pouch minimizes the possibility of fecal matter contacting and clogging the filter material or escaping through apertures 21, and the bar weld prevents any carbon that flakes from filter 11 from contacting the stoma.

Front and rear pouch panel laminates are preferably both formed from water repellent tissue paper and hot water soluble polyvinyl alcohol film joined by a polyurethane adhesive according to well known laminating procedures. The hot water soluble polyvinyl alcohol films 18 and 34 are selected so as to dissolve in water at a temperature of from about 140° F. to about 200° F., preferably about 160° F. Thus, the film materials 18 and 34 will not dissolve at body temperature and will remain intact in the presence of perspiration or moisture that might seep through the tissue paper layers 19 and 33.

The water resistant tissue paper layers 19 and 33 provide strength for the pouch. These paper layers prevent or at least sufficiently reduce the rate at which moisture from outside the pouch such as body perspiration will contact the hot water soluble film layers. Also, the tissue paper on the front panel provides a more pleasant feel against the body than conventional polymeric ostomy pouch film. The use of hot water soluble polyvinyl alcohol film material for layers 18 and 34 prevents the pouch from dissolving or bleeding through due to moisture within the fecal material collected in the pouch. Also, the hot water soluble polyvinyl alcohol film material maintains its structural integrity in the presence of small amounts of water or perspiration that may pass through the outer water resistant tissue paper layer.

The preferred laminate structure of water resistant tissue paper and hot water soluble polyvinyl alcohol results in a pouch having adequate odor barrier properties during the normal period of use in contrast to polyvinyl alcohol films which themselves lose their odor barrier properties when wet. Of course, the tissue paper prevents skin discomfort normally associated with direct contact with polyvinyl alcohol films. Also, the laminate structure results in a pouch that maintains its structural integrity under a range of use conditions whereas pouches formed only of hot water soluble polyvinyl alcohol will distort under load.

The interior surfaces of the hot water soluble polyvinyl alcohol films 18 and 34 are preferably coated or dusted with corn starch. This prevents or reduces the tendency of these film layers to seal together when the pouches are stored overtime in a package. The corn starch also apparently increases the slip between the hot water soluble polyvinyl alcohol film and the fecal material entering the pouch so that the material will more readily pass to the bottom of the pouch away from the stoma. Preferably, the dusting is done just prior to the joining of the front and rear pouch panels.

A suitable commercially available water resistant tissue paper for use as layers 19 and 33 is sold by the James River Corporation of Gouverneur, N.Y. under their code 35707. A suitable commercially available hot water soluble polyvinyl alcohol for use as layers 18 and 34 in front panel laminate 12 and rear panel laminate 32 as well as for optional adhesive backing layer 23 is available from the Mono-Sol Division of Chris-Craft Industrial Products under their code PVA 1000. This material becomes soluble in water heated to a temperature of above 160° F. The laminate preferably consists of a single ply of water resistant tissue paper and a film of hot water soluble polyvinyl alcohol of from about 0.5 to about 2.0 mils thickness. More preferably, the hot water soluble polyvinyl alcohol will be a film of from about 0.8 to about 1.25 mils thickness.

Figure 8:
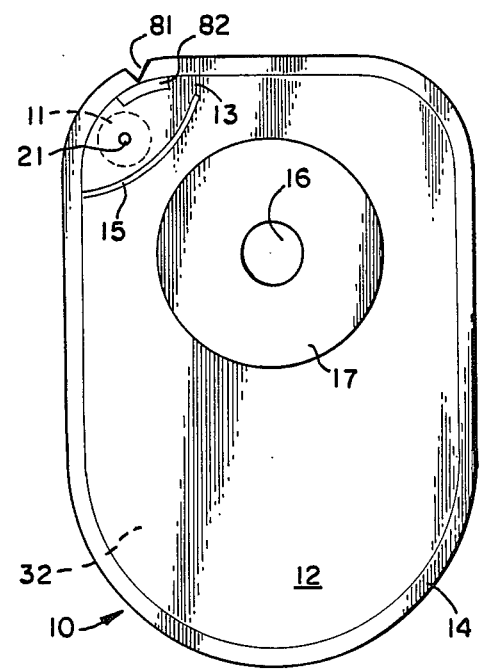
FIG. 8 is a front view of an ostomy pouch similar to that shown in FIG. 2 but including means to permit the pouch to be torn prior to disposal.

The pressure sensitive adhesive layer 24 preferably consists of one or more water soluble or swellable hydrocolloids homogeneously dispersed in polyisobutylene as taught by Chen in U.S. Pat. No. 3,339,546. Other suitable hydrocolloid containing pressure sensitive adhesive compositions are taught by Doyle et al. in U.S. Pat. No. 4,551,490. The adhesive mass 24 is preferably extruded between two sheets of silicone coated release paper 25, embodiment of FIG. 4, or is extruded onto a single sheet of silicone coated release paper 25 and overlayed with backing film layer 23, embodiment of FIG. 5. When cooled, this adhesive faceplate is die cut to the circular shape with starter hole 16 as shown in FIGS. 2, 3 and 8 or is die cut to include tabs 26 and starter hole 16 as shown in FIG. 7. Of course, the configuration of the adhesive faceplate can be varied from those shown in the drawings. Preferably, adhesive layer 24 is from about 25 to about 35 mils thickness. Backing film layer 23, if present, is from about 0.8 to about 1.5 mils thickness.

The configuration of the ostomy pouch 10 can also be varied from the general eliptical shape shown in the figures. In general, the pouch will vary in width from about 4 to about 6 inches and in length from about 7 to about 10 inches so as to accomodate up to about 300 g. of stomal discharge. The pouch could also be constructed in a smaller size for pediatric use. Of course, instead of the closed end pouch construction shown in the figures, the same laminates could be employed to construct a flushable pouch having a drainable narrow open ended tail portion. This tail portion would then be sealed with a conventional clip type closure during usage. This clip could be flushable if made of an appropriate water soluble material such as polyethylene oxide. If made from conventional materials such as polyethylene, then the clip would not be flushed with the pouch at the time of disposal.

The flushable ostomy pouch 10 can be assembled in an automated fashion. For example, a countinuous web of the front panel laminate 12 is advanced with film layer 18 on the top. In the first operation, starter hole 16 and one or more apertures 21 are cut or punched out. In a second operation, the filter material 11 is attached to the front panel laminate. This is done by cutting the filter to shape, preferably a circular shape as shown in FIGS. 2 and 3, and coating one surface with a heat activatable adhesive. In fact, certain commercially available activated carbon filter materials come already coated with an adhesive so that after cutting to shape all that is required is the removal of a sheet of release paper. The filter 11 is then pressed against the hot water soluble film layer 18 by a heated surface which bonds the filter in place overlying aperture 21.

At the same time, an adhesive faceplate assembly is cut to shape with a starter hole 16. The faceplate can be cut to the circular pattern shown in FIGS. 2, 3 and 8 or to the pattern including ear flaps 26 shown in FIG. 7. The adhesive assembly as shown in FIG. 4 having one surface covered with release paper is then passed under the web of front panel laminate 12 so that the starter holes 16 are aligned. An air piston tool having a circular shaped heat transfer surface is pressed down against film 18 thus forming a heat seal between layer 19 and adhesive layer 24. Of course, in the embodiment of FIG. 7, the area of adhesive 24 outside the periphery of the heat seal bond 27 would bond adhesively to the outer layer 19 of the front panel. However, the user will be able to peel the adhesive material away from the front panel in this area at the time of application of the pouch to the body.

When an adhesive assembly 17 including a backing layer 23 as shown in FIG. 5 is employed, the procedure is slightly different. The adhesive faceplate assembly is moistened by spraying water onto the exposed surface of film layer 23 or treating such surface with water vapor. The moistened faceplate assembly is then passed under the web of front panel laminate 12 so that the starter holes 16 are aligned. An air piston type tool having a circular shaped heat transfer surface is pressed down against film 18 thus forming a heat seal between layers 23 and layer 19. Alternatively, the surface of layer 19 which is to contact the faceplate assembly can be moistened by spraying with water. In either case, the presence of moisture enables the use of high enough temperature, i.e., about 425° F., so as to form a true heat seal between layers 19 and 23. Of course, in the embodiment of FIG. 7 in which backing layer 23 is present, there would be no bond between layer 23 and front panel outer layer 19 outside the periphery of the heat seal bond 27.

The resulting front panel web is mated with a web of the rear panel laminate 32 so that film layers 18 and 34 are facing one another. A powdery atmosphere of corn starch is released so as to coat or dust the facing surfaces of layers 18 and 34. A continuous heat seal is made joining the two panels to form the pouch periphery 14 while at the same time the panels are also joined along the arc line 15 leaving a gap 13. In the next operation the completed pouch is cut from the web. Of course, the order of the operations described above can be varied. For example, the filter could be attached to the rear panel, or the pouch could be outlined sealed and cut from the web in the same operation.

The ostomy pouch 10 has been shown as having an adhesive means for attachment to the body. However, attaching means 17 could be a mechanical structure of polymeric material adapted to releasably couple the pouch to an adhesive pad secured to the body. This body side pad would be provided with a mechanical structure that couples with the structure on the pouch. Such a mechanical two-piece ostomy coupling system is shown by Steer, et al. in U.S. Pat. No. 4,460,363. Thus, the polymeric channel shaped bag coupling element of Steer, et al. could be affixed to front panel 12 around starter hole 16 by adhesive or other means. Such a pouch would be flushable if the channel shaped coupling element is made of an appropriate water soluble material such as, for example, polyethylene oxide.

The flushability of the pouch 10 can be enhanced by impregnating water resistant tissue paper layer 19 as well as layer 33 if it is also formed from water resistant tissue paper with one or more surfactants and/or softening agents. These materials upon contact with the water in the toilet bowl function to increase the rate at which the hot water soluble film layers are softened by the water and in addition provide added lubrication. Suitable materials for this purpose are as listed above.

The pouch 10 is disposed of by flushing in a conventional toilet. Preferably, the pouch and its contents are first placed within disposal bag 60. This should be done in a manner so as to avoid entrapping air within the pouch. One way to do this is to place the unfolded used ostomy pouch completely into the disposal bag bottom first, leaving the unsealed end of the disposal bag open. The disposal bag with the enclosed ostomy pouch is then placed into the water within the toilet bowl so that the stomal aperture 16 faces upward and is near the front of the bowl. The toilet is then flushed. While in the toilet bowl the outer disposal bag 60 immediately begins to soften and dissolve to a slimy mass. This creates a completely lubricated outer surface on the used flexible ostomy pouch 10. The ostomy pouch then easily passes from the bowl, through the trap, and enters the waste line. The vortex created by flushing is sufficient to carry the disposal bag containing the ostomy pouch and its contents through a conventional household plumbing system. With empty or very lightly loaded pouches it may be desirable to press the gas out of the pouch or puncture or cut the pouch in the area above the stomal opening prior to placement in the disposal bag so as to provide an additional exit for entrapped air. When toilets of a non vortex, washdown type are used, it is also desirable to cut or puncture the pouch in the area above the stomal opening. Over time, layers 18, 19, 23 (if present), 33, and 34 as well as adhesive mass 24 will eventually disintegrate in a septic system.

Rather than cutting or puncturing pouch 10 to release entrapped air, pouch 10 could be provided with an integral tear strip in either the front or rear panel laminates. Preferably, such tear strip would be located just beneath the heat seal 14 at the top edge of the pouch, to the side of gap 13. Such a tear strip could be constructed by embedding a string within film layer 18 which partially extends through layer 19. The tear created should have a jagged edge since a smooth edge has a tendency to reseal when the pouch becomes wet following placement in the toilet bowl.

Another way of accomplishing this result is to include a V-shaped notch in the area of the top peripheral heat seal. Such a notch is shown as the numeral 81 in FIG. 8. The notch provides an area of weakness which the user can employ to create a jagged tear across the top of the pouch prior to disposal. A heat seal bond 82 extends below the notch to insure the integrity of the peripheral weld 14. Notch 81 and seal 82 can be made at the same time as peripheral weld 14.

The following examples are illustrative of the invention.

EXAMPLE I

Pouches having the general configuration shown in FIGS. 2, 3, 5, and 6 are prepared as follows. Front and rear panels are each a laminate of a single ply of water resistant tissue paper (James River Corp., 35707) laminated by polyurethane adhesive to a 1.1 mil. thick film of hot water soluble polyvinyl alcohol (Mono-Sol PVA 1000). The laminates are, of course, sealed together so that the polyvinyl alcohol film layers form the interior pouch surface. The stomal opening 16 is approximately 18 mm. in diameter.

The adhesive attaching means 17 consisting of a layer of pressure sensitive adhesive 24 and a backing film layer 23 is prepared as follows.

Layer 24 consists on a weight percent basis of the following ingredients:

Sodium carboxymethylcellulose: 22.17
Gelatin: 22.17
Pectin: 22.16
Polyisobutylene(available from Exxon as Vistanex LM-MH): 9.5
Polyisobutylene(available from Exxon as Vistanex L-100): 9.5
Mineral oil: 14.5

A premix of the two grades of polyisobutylene is prepared by masticating the L-100 to a fine shred in a Sigma blade mixer and blending with the LM-MH. A weighted amount of this premix is then placed into a mixer and a powdery blend of the gelatin, pectin, and sodium carboxymethylcellulose is added. Mixing is continued and the mineral oil is gradually added and incorporated into the mass. The mass is heated to 80°-90° C. and extruded between a sheet of silicone coated release paper and 1.5 mils thick film of hot water soluble polyvinyl alcohol (Mono Sol PVA 1000). The adhesive is of a thickness of about 25 mils. The resulting attaching means 17 is cut into shape with an opening corresponding to stomal aperture 16 and affixed to the tissue paper layer of the pouch front panel by a combination of moisture, heat and pressure.

Bag 60 as shown in FIG. 1 is constructed by folding a sheet of embossed cold water soluble polyvinyl alcohol film (6 inch by 8 inch of 15 micron thick film of Hi-Selon AH-15 from Nippon Gohsei) over on itself and heat sealing the side edges to leave a 6 inch open mouth. No holes are present in the bag walls.

In these experiments, the pouches are filled with 150 grams of a blend of meat type dogfood and agar to simulate fecal material. The pouches are flushed in various toilet systems both by merely placing the pouch 10 in the toilet bowl by itself and by first placing the pouch within a bag 60 and then placing the combination in the toilet bowl. The toilet is flushed immediately after the pouch or bag containing pouch is placed therein. The pouch is considered to have successfully flushed if it passes from the bowl and trap in three flushes or less and a failure if the water rises to or beyond the level of the rim of the toilet or the pouch fails to clear the bowl and trap after the third flush. Also, noted are any instances of transient blockage of the pouch in the toilet system which clears due to increased head from water back up in the bowl, i.e., spontaneous release.

TOILET SYSTEMS

| | American Standard Syphen Vortex (3.5 gallon tank) | | Mansfield Syphon Jet (3.5 gallon tank) | | Douglas-Leader Washdown Syphon Jet (5 gallon tank) | | Manfield Quantum Water Saver (1.4 gallon jet flush) | | American Standard Roma (Low Boy, 3.5 gallon tank) | |
|---|---|---|---|---|---|---|---|---|---|---|
| | Pouch alone | Pouch within bag | Pouch alone | Pouch within bag | Pouch alone | Pouch within bag | Pouch alone | Pouch within bag | Pouch alone | Pouch within Bag |
| Pouches Passed/Pouches Attempted | 15/20 | 25/25 | 6/23 | 37/37 | 18/20 | 21/21 | 3/6 | 11/12 | 19/31 | 30/30 |
| In the successes, the number requiring multiple flushes to clear bowl and trap | 1 pouch required 2 flushes | 1 pouch-bag combination required 2 flushes | 2 pouches required 2 flushes | 0 | 2 pouches required 2 flushes | 3 pouch-bag combinations required 2 flushes | 1 pouch required 2 flushes and 1 pouch required 3 flushes | 2 pouch-bag combinations required 2 flushes | 1 pouch required 2 flushes | 0 |
| Successes with spontaneous release | 2 | 0 | 2 | 2 | 5 | 0 | 0 | 3 | 7 | 2 |

EXAMPLE II

Pouches 10 and bags 60 are prepared identically to those described in Example I except that bag 60 has three apertures punched through both bag walls. In these experiments, the load within the pouches are varied.

MANSFIELD SYPHON JET (3.5 gallon tank)

| | POUCH ALONE | | | POUCH-BAG COMBINATION | | |
|---|---|---|---|---|---|---|
| Load | Pass rate | Number of passes requiring multiple flushes | Number of passes with spontaneous release | Pass Rate | Number of passes requiring multiple flushes | Number of passes with spontaneous release |
| 250 g. | — | — | — | 2/3 | 1 pouch-bag combination required flushes | 2 |
| 200 g. + 50 cc. of water | — | — | — | 5/5 | 0 | 0 |
| 225 g. | — | — | — | 10/10 | 0 | 2 |
| 200 g. | — | — | — | 10/10 | 0 | 5 |
| 175 g. | — | — | — | 10/10 | 0 | 2 |
| 150 g. | 6/23 | 2 pouches required 2 flushes | 2 | 10/10 | 0 | 0 |
| 50 g. | — | — | — | 10/10 | 3 pouch-bag combinations required 2 flushes | 0 |
| 25 g. | — | — | — | 10/10 | 2 pouch-bag combinations required 2 flushes | 0 |
| 12 g. | — | — | — | — | — | — |
| 0 g. | 5/5 (inflated) | 4 pouches required 2 flushes, 1 pouch required 3 flushes | 0 | 5/5 (inflated) | 3 pouch-bag combinations required 2 flushes (two noticeable backups) | 0 |
| | | | | 5/5 (air pressed out) | 1 pouch-bag combination required 2 flushes | 0 |

| | DOUGLAS-LEADER WASHDOWN SYPHON JET (5 Gallon tank) | | | | | |
|---|---|---|---|---|---|---|
| | POUCH ALONE | | | POUCH-BAG COMBINATION | | |
| Load | Pass rate | Number of passes requiring multiple flushes | Number of passes with spontaneous release | Pass rate | Number of passes requiring multiple flushes | Number of passes with spontaneous release |
| 150 g. | 18/20 | 2 pouches required 2 flushes | 0 | 10/10 | 1 pouch-bag combination required 2 flushes | 0 |
| 25 g. | — | — | — | 10/10 | 1 pouch-bag combination required 2 flushes, 1 pouch-bag combination required 3 flushes | 0 |
| 12 g. | — | — | — | 12/13 (air not pressed out) | 3 pouch-bag combinations required 2 flushes, 1 pouch-bag combination required 3 flushes | 0 |
| 0 | — | — | — | 9/10 (air pressed out) | 3 pouch-bag combinations required 2 flushes | 0 |

| | AUSTROVIT P TRAP BOWL (no vortex washdown, turbulent flush, about 3 inches of water in bowl), equipped with Gebberit 9 liter, plug type valve tank | | | | | |
|---|---|---|---|---|---|---|
| | POUCH ALONE | | | POUCH-BAG COMBINATION | | |
| Load | Pass rate | Number of passes requiring multiple flushes | Number of passes with spontaneous release | Pass rate | Number of passes requiring multiple flushes | Number of passes with spontaneous release |
| 150 g | 13/13 | 0 | 0 | 3/3 | 0 | 0 |
| 25 g | 3/3 | 0 | 0 | 1/1 | 0 | 0 |
| 12 g | 1/1 | 1 pouch required 3 flushes | 0 | 4/4 | 3 pouch-bag combinations required 3 flushes | 0 |
| 0 | 0/2 | | | 0/2 (inflated) | | |
| 0 | 1/1 (air pressed out) | 1 pouch required 2 flushes | 0 | 3/3 (air pressed out) | 2-pouch-bag combinations required 2 flushes | 0 |

EXAMPLE III

Pouches are prepared from the front and rear panel laminates and adhesive attaching means described in Example I except that the attaching means is of alternate configuration shown in FIG. 7. Bags 60 are prepared as described in Example II, i.e., with three apertures. In these experiments the load within the pouches are varied.

| | AMERICAN STANDARD SYPHON VORTEX (3.5 gallon tank) POUCH-BAG COMBINATION | | | MANSFIELD SYPHON JET (3.5 gallon tank) POUCH BAG COMBINATION | | |
|---|---|---|---|---|---|---|
| Load | Pass rate | Number of passes requiring multiple flushes | Number of passes with spontaneous release | Pass rate | Number of passes requiring multiple flushes | Number of passes with spontaneous release |
| 150 g. | 3/3 | 0 | 0 | 5/5 | 0 | 0 |
| 50 | — | — | — | 5/5 | 2 pouch-bag combinations required 2 flushes | 0 |
| 25 g. | — | — | — | 4/4 | 0 | 0 |
| 0 | 3/3 | 1 pouch-bag combination required 2 flushes | 0 | 5/5 (air pressed out) | 4 pouch-bag combinations required 2 flushes 1 pouch-bag combination required 3 flushes | 0 |

EXAMPLE IV

In this experiment, a commercially available colostomy pouch with an 18 mm. opening (ConvaTec's Active Life One Piece Closed-End Pouch With Skin Barrier) constructed from front and rear panels of a triple laminate composed of an outer and inner layer of ethylene vinylacetate and a core of a copolymer of vinyl chloride and polyvinylidene chloride containing a load of 150 g. is placed within a bag 60 constructed as described in Example II with three apertures, and flushed in a Mansfield Syphon Jet (3.5 gallon tank) system. The pouch-bag combination flushed on the first try. However, there was spontaneous release, i.e., transient blockage which cleared due to increased head from water backup in the bowl.

EXAMPLE V

In this experiment, pouches are constructed as described in Example I, filled with 150 g. load, wrapped within an embossed warm water soluble polyvinyl alcohol film (1 mil. thick, Hi-Selon H-25 available from Nippon Gohsei Company), and flushed in an American Standard Roma (Low Boy, 3.5 gallon tank) toilet system. Two runs were made and both wrapped pouches were flushed on the first try with no spontaneous release noted.

EXAMPLE VI

In this experiment, pouches are constructed as described in Example I. The empty pouches are placed within a sleeve formed by heat sealing a sheet of embossed cold water soluble polyvinyl alcohol film (6 inch by 8 inch of 15 micron thick film of Hi-Selon AH-15 from Nippon Gohsei) so that both 6 inch sides remain open. Three runs were made by flushing the empty pouch-sleeve combination in a Mansfield Syphon Jet (3.5 gallon tank) system. Two pouch-sleeve combinations required two flushes and the other required three flushes to clear the bowl and trap. No instances of spontaneous release were noted.

EXAMPLE VII

In this experiment, pouches are constructed as described in Example I except that no filter element 11 is included and the stomal opening 16 is 38 mm. in diameter. Each pouch is filled with a load of 150 g. and aged overnight. The filled pouch is then placed in the bowl of a Mansfield Syphon Jet (3.5 gallon tank) and a measured quantity of surfactant and/or softening agent is added one minute prior to flushing.

| Surfactant and/or softening agent | Amount used | Pass rate | Number of passes requiring multiple flushes | Number of passes with spontaneous release |
|---|---|---|---|---|
| none | — | 18/34 | 10 pouches required 2 flushes | 6 |
| glycerine | 15 cc. | 3/3 | 1 pouch required 2 flushes | 1 |
| 1:1 stearic acid monoethanolamide (available from Mona Ind. as Monamid S) | about 15 g. | 6/6 | | 3 |
| Ivory ® dishwashing liquid (Proctor and Gamble, U.S. Pat. No. 3,793,233) | 15 cc | 8/10 | 3 pouches required 2 flushes, 1 pouch required 3 flushes | 4 |
| | 30 cc | 4/4 | 1 pouch required 3 flushes | 3 |
| Joy ® dishwashing liquid (Proctor & Gamble, U.S. Pat. No. 4,133,779 and 4,316,824) | 5 cc | 4/5 | 3 pouches required 2 flushes | 1 |
| | 15 cc | 26/29 | 6 pouches required 2 flushes | 5 |
| Monaterge LF-945 (a blend of nonionic, amphoteric surfactants available from Mona Ind.) | 5 cc | 3/5 | — | 2 |
| | 15 cc | 16/18 | 5 pouches required 2 flushes | 7 |

What is claimed is:

1. An ostomy pouch which can be disposed of by flushing in a conventional toilet bowl comprising a front panel formed of a laminate of a film of water swellable, cold water insoluble, hot water soluble polyvinyl alcohol and water resistant tissue paper and a rear panel formed of a laminate of a film of water swellable, cold water insoluble, hot water soluble polyvinyl alcohol and either water resistant tissue paper or a film of cold water soluble polyvinyl alcohol both of which are relatively friction free when contacted with the clothing of the user, said front and rear panels joined together over a majority of their periphery to form said ostomy pouch, said front and rear panels oriented so that said films of hot water soluble polyvinyl alcohol constitute the pouch interior, said front panel having an opening therethrough that can fit or can be enlarged to fit around the stoma, and attachment means secured to said front panel around said stomal opening for attachment of said pouch to the body of the user wherein said pouch is capable of maintaining its structural integrity during the period of use.

2. The pouch of claim 1 wherein said front and rear panel laminates both are formed of a film of hot water soluble polyvinyl alcohol of from about 0.5 to about 2.0 mils. thickness and a single ply of water resistant tissue paper laminated together by a polyurethane adhesive.

3. The pouch of claim 1 wherein said hot water soluble polyvinyl alcohol films are from about 0.8 to about 1.25 mils thickness.

4. The pouch of claim 1 wherein said attachment means comprises a layer of pressure sensitive adhesive secured directly to the water resistant tissue paper layer of said front panel, and wherein said adhesive layer includes an opening substantially similar to said front panel stomal opening that fits or can be enlarged to fit around the stoma.

5. The pouch of claim 4 wherein the exposed surface of said adhesive layer is covered by a sheet of release paper prior to use.

6. The pouch of claim 4 wherein said layer of pressure sensitive adhesive has an outer periphery of a generally circular shape and is sealed by heat and pressure across its entire surface area to the water resistant tissue paper layer of said front panel.

7. The pouch of claim 4 wherein said layer of pressure sensitive adhesive includes one or more portions which extend beyond the area sealed by heat and pressure to the water resistant tissue paper layer of said front panel.

8. The pouch of claim 4 wherein said attachment means comprises a layer of pressure sensitive adhesive and a backing film, said backing film secured directly to the water resistant tissue paper layer of said front panel, and wherein said adhesive layer and said backing film include an opening substantially similar to said front panel stomal opening that fits or can be enlarged to fit around the stoma.

9. The pouch of claim 8 wherein the exposed surface of said adhesive layer is covered by a sheet of release paper prior to use.

10. The pouch of claim 9 wherein said attaching means is secured over its entire surface area to said front panel.

11. The pouch of claim 9 wherein one or more peripheral portions of said attaching means extend beyond the area in which said attachment means is secured to said front panel.

12. The pouch of claim 1 wherein said front and rear panels are joined together around their entire periphery to form a closed ended pouch.

13. The pouch of claim 12 wherein a filter means is provided in the pouch above the stomal opening in the front panel when the pouch is attached to a user.

14. The pouch of claim 13 wherein said filter means contains activated carbon.

15. The pouch of claim 14 wherein said front and rear panels are joined in the area around said filter means so as to isolate said filter from the remaining portion of said pouch except for a gap adjacent the peripheral seal at the top edge of the pouch which permits gas to flow from the pouch to the filter means and prevents contact of the stoma with carbon material flaking from said filter.

16. The pouch of claim 15 wherein said filter means is adhesively secured to one of said panels and one or more perforations are present in the portion of one of said panels overlaying said filter means.

17. The pouch of claim 1 wherein one or both of said water resistant tissue paper layers are impregnated with a surfactant.

18. The pouch of claim 1, wherein a notch is provided in a portion of the peripheral bond between said front and rear panels at the top edge of said pouch, said notch enabling the pouch after use to torn open across the top prior to disposal.

19. The pouch of claim 1 wherein a tear strip is provided in either the front or rear panel near the top edge of said pouch, said tear strip enabling the pouch after use to be torn open across the top prior to disposal.

20. The method of disposing of a used ostomy pouch constructed in accordance with claim 19 comprising removing said pouch from the body, placing said pouch in a toilet bowl, contacting the exposed pouch surface in the toilet bowl with a surfactant containing composition, and flushing whereby the pouch and its contents will pass from the bowl.

21. The method of claim 20 wherein the pouch is perforated, cut, or torn after removal from the body in the area above the stomal opening prior to placement in the toilet bowl.

22. The method of improving the flushability of an ostomy pouch constructed in accordance with claim 19 in marginally performing or clog prone toilets by adding a surfactant and/or softening composition to the water in the toilet bowl or to the cistern feeding the toilet bowl prior to disposal of the ostomy pouch.

23. The method of disposing of a used ostomy pouch constructed in accordance with claim 19 comprising removing said pouch from the body, wrapping or completely enclosing said pouch within a material that becomes slimy or exudes a slimy material when in contact with the water in a toilet bowl, placing said wrapped or enclosed pouch into a toilet bowl, and flushing whereby said pouch and its contents pass from said bowl through the trap into the waste line.

24. The method of claim 23 wherein the pouch is perforated, cut or torn after removal from the body and prior to wrapping or enclosing within said material.

25. The method of claim 23 wherein said ostomy pouch is placed within a bag or sleeve formed from highly absorbent tissue paper.

26. The method of claim 23 wherein said ostomy pouch is placed with a bag or sleeve formed from cold water soluble polyvinyl alcohol.

27. The method of claim 26 wherein said ostomy pouch is placed with a bag formed from an embossed cold water soluble polyvinyl alcohol film of about 0.6 mils. thickness.

28. The method of claim 27 wherein said bag has one or more apertures to aid in the release of entrapped air.

29. The method of claim 23 wherein said ostomy pouch is placed within a bag or sleeve formed from tissue paper impregnated with a surfactant and/or softening agent.

30. The method of disposing of a used ostomy pouch comprising removing said pouch from the body, wrapping or completely enclosing said pouch within a material that becomes slimy or exudes a slimy material when in contact with the water in a toilet bowl, placing said wrapped or enclosed pouch into a toilet bowl, and flushing whereby said pouch and its contents pass from said bowl through the trap into the waste line.

31. The method of claim 30 wherein said ostomy pouch is placed within a bag or sleeve formed from highly absorbent tissue paper.

32. The method of claim 30 wherein said ostomy pouch is placed within a bag or sleeve formed from cold water soluble polyvinyl alcohol.

33. The method of claim 32 wherein said ostomy pouch is placed within a bag formed from an embossed cold water soluble polyvinyl alcohol film of about 0.6 mils thickness.

34. The method of claim 33 wherein said bag has one or more apertures to aid in the release of entrapped air.

35. The method of claim 30 wherein said ostomy pouch is placed within a bag or sleeve formed from tissue paper impregnated with a surfactant and/or softening agent.

* * * * *

UNITED STATES PATENT AND TRADEMARK OFFICE
CERTIFICATE OF CORRECTION

PATENT NO. : 4,762,738
DATED : August 9, 1988
INVENTOR(S) : Denis E. Keyes et al.

It is certified that error appears in the above-identified patent and that said Letters Patent is hereby corrected as shown below:

Col. 17, line 38 -- "19" should be -- 1 --.
Col. 17, line 49 -- "19" should be -- 1 --.
Col. 18, line 2 -- "19" should be -- 1 --.

Signed and Sealed this

Twenty-second Day of August, 1989

Attest:

DONALD J. QUIGG

Attesting Officer

Commissioner of Patents and Trademarks